US007288270B1

United States Patent
Sekharam et al.

(10) Patent No.: US 7,288,270 B1
(45) Date of Patent: Oct. 30, 2007

(54) THERAPEUTIC COMPOSITION FOR THE PREVENTION AND TREATMENT OF MUCOSITIS AND MUCOSAL DISORDERS

(76) Inventors: Kotha S. Sekharam, 8730 Ashworth Dr., Tampa, FL (US) 33647; Madhavi K. Sekharam, 9702 Treetops lake Rd., Tampa, FL (US) 33626

( * ) Notice: Subject to any disclaimer, the term of this patent is extended or adjusted under 35 U.S.C. 154(b) by 0 days.

(21) Appl. No.: 11/407,823

(22) Filed: Apr. 20, 2006

Related U.S. Application Data

(63) Continuation-in-part of application No. 10/158,481, filed on May 30, 2002, now abandoned.

(51) Int. Cl.
*A01N 65/00* (2006.01)

(52) U.S. Cl. .................................................. 424/725
(58) Field of Classification Search ............... None
See application file for complete search history.

(56) References Cited

U.S. PATENT DOCUMENTS

| 6,207,164 | B1 * | 3/2001 | Kreuter et al. ............... 424/725 |
| 6,348,200 | B1 * | 2/2002 | Nakajima et al. ............ 424/401 |
| 2002/0187166 | A1 * | 12/2002 | Ishikawa et al. ............ 424/401 |
| 2004/0001817 | A1 * | 1/2004 | Giampapa ................... 424/94.1 |

* cited by examiner

*Primary Examiner*—Michael Meller
(74) *Attorney, Agent, or Firm*—Edward P. Dutkiewicz

(57) ABSTRACT

A therapeutic composition of deglycyrrizinated *glycyrrhiza* extract, *Centella* extract, Angelica Root extract, green tea extract, stilbene, and *Aloe* extract.

13 Claims, No Drawings

THERAPEUTIC COMPOSITION FOR THE PREVENTION AND TREATMENT OF MUCOSITIS AND MUCOSAL DISORDERS

RELATED APPLICATION

The present application is a continuation-in-part of a previously filed application having Ser. No. 10/158,481, filed on May 30, 2002 now abandoned. This application claims the priority of the above described parent patent application.

BACKGROUND OF THE INVENTION

1. Field of the Invention

The present invention relates to a therapeutic composition for the prevention and treatment of mucositis and mucosal disorders, and more particularly pertains to a therapeutic composition for the prevention and treatment of mucositis and mucosal disorders.

2. Description of the Prior Art

The use of other known methods of treating oral mucositis, and mucositis in general, is known in the prior art. More specifically, other known methods of treating oral mucositis, and mucositis in general, previously devised and utilized for the purpose of reducing mucosal inflammation are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,972,906 issued to Asculai, et al. discloses a method for the treatment of mucous membrane trauma disease for the relief of pain associated therewith by administering topically a compound with non-steroidal anti-inflammatory drug and a form of hyaluronic acid.

U.S. Pat. No. 5,545,668 issued to Skubitz, et al. discloses a method of treating oropharyngeal mucositis by administering orally, an amino acid, glutamine. U.S. Pat. No. 5,945,089 issued to Libin discloses a method to alleviate symptoms of mucositis by using Triclosan. U.S. Pat. No. 6,025,326 issued to Steinberg, et al. discloses a method to prevent and treat oral mucositis by using an antimicrobial peptide, protegrin peptide. U.S. Pat. No. 6,274,601 issued to Cullinan discloses a method of inhibiting ulcerative mucositis by using a select group of 2-phenyl-3-aroylbenzothiophenes. U.S. Pat. No. 5,788,982 issued to Nadoolman discloses a method and composition for treating oral pain using 5-9 ppm capsaicin in a candy vehicle.

U.S. Pat. No. 6,110,891 issued to Pusztai et al discloses a method for the control of mucosal cell proliferation using lectins. Lectins are known to be detrimental to the metabolism of animals at higher doses; may interfere with the thymus, cause hypertrophy of the pancreas.

While these devices and methods fulfill their respective, particular objectives and requirements, the aforementioned patents do not describe therapeutic composition for the prevention and treatment of mucositis and mucosal disorders that allows treating oral mucositis with a new combination of therapeutic agents.

In this respect, the therapeutic composition for the prevention and treatment of mucositis and mucosal disorders, according to the present invention, substantially departs from the conventional concepts and designs of the prior art, and in doing so provides an apparatus primarily developed for the purpose of treating oral mucositis with a new combination of therapeutic agents.

Therefore, it can be appreciated that there exists a continuing need for a new and improved therapeutic composition for the prevention and treatment of mucositis and mucosal disorders which can be used for treating oral mucositis with a new combination of therapeutic agents. In this regard, the present invention substantially fulfills this need.

SUMMARY OF THE INVENTION

In view of the foregoing disadvantages inherent in the known types of other known methods of treating oral mucositis, and mucositis in general now present in the prior art, the present invention provides an improved therapeutic composition for the prevention and treatment of mucositis and mucosal disorders. As such, the general purpose of the present invention, which will be described subsequently in greater detail, is to provide a new and improved therapeutic composition for the prevention and treatment of mucositis and mucosal disorders and method which has all the advantages of the prior art and none of the disadvantages.

To attain this, the present invention essentially comprises a therapeutic composition for the prevention and treatment of mucositis and mucosal disorders of areas of the body protected by mucous membranes, including the gastrointestinal tract, the respiratory tract, the urinary tract, and the reproductive system, with the composition comprising several components, in combination.

First provided is a stilbene compound.

Next provided is a deglycyrrhizinated *glycyrrhiza* extract obtained from the deglycyrrhizinated *glycyrrhiza* extracts. These extracts include *Glycyrrhiza Glabra*, *G. Kansuesis*, and *G. Inflata*. Next provided is a *Centella* extract. The *Centella* extract is obtained from a source which is a member of the group of sources that includes asiaticoside, madecaccoside, centelloside, centoic acid and centellic acid.

Next provided is a polyphenol-rich plant extract which is obtained from the group of polyphenol-rich plant extracts which includes the *Camellia* species. The *Camellia* species is a source of purified polyphenol. Purified phenol is a member of the group of purified phenol that includes (−) Epicatechin, (−) Epigallocatechin, (−) Epicatechin gallate, and (−) Epigallocatechin gallate.

Lastly provided is an *Aloe Vera* extract. The *Aloe Vera* extract is obtained from a member of the group of botanical sources of *Aloe Vera* extract that includes *A. barbadensis*, *A. vulgare*, *A. arborescens*, *A. ferox*, and *A. perryi*.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved therapeutic composition for the prevention and treatment of mucositis and mucosal disorders which has all of the advantages of the prior art, including other known methods of treating oral mucositis and mucositis in general, and none of the disadvantages.

It is another object of the present invention to provide a new and improved therapeutic composition for the prevention and treatment of mucositis and mucosal disorders which may be easily and efficiently manufactured and marketed.

It is further object of the present invention to provide a new and improved therapeutic composition for the prevention and treatment of mucositis and mucosal disorders which is of durable and reliable constructions.

An even further object of the present invention is to provide a new and improved therapeutic composition for the prevention and treatment of mucositis and mucosal disorders which is susceptible of a low cost of manufacture with regard to both materials and labor, and which accordingly is then susceptible of low prices of sale to the consuming public, thereby making such therapeutic composition for the prevention and treatment of mucositis and mucosal disorders economically available to the buying public.

Even still another object of the present invention is to provide a therapeutic composition for the prevention and treatment of mucositis and mucosal disorders for treating oral mucositis with a new combination of therapeutic agents.

Lastly, it is an object of the present invention to provide a new and improved therapeutic composition comprising several components, in combination. Those components are deglycyrrizinated *glycyrrhiza* extract, *Centella* extract, Angelica Root extract, green tea extract, Stilbene, and *Aloe* extract.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

DESCRIPTION OF THE PREFERRED EMBODIMENT

The preferred embodiment of the new and improved therapeutic composition for the prevention and treatment of mucositis and mucosal disorders, embodying the principles and concepts of the present invention, will be described.

The present invention, the therapeutic composition for the prevention and treatment of mucositis and mucosal disorders is comprised of a plurality of components. Such components in their broadest context deglycyrrizinated *glycyrrhiza* extract, *Centella* extract, Angelica Root extract, green tea extract, stilbene, and *Aloe* extract. Such components are individually configured and correlated with respect to each other so as to attain the desired objective.

A therapeutic composition for the prevention and treatment of mucositis and mucosal disorders of areas of the body protected by mucous membranes, including the gastrointestinal tract, the respiratory tract, the urinary tract, and the reproductive system, with the composition comprising several components, in combination.

First provided is a stilbene compound. Stilbenes (stilbenoids) have recently received great attention due to various biotherapeutic effects, including antioxidant, fungistatic, cardioprotective, and anticancer properties.

Polyhydroxylated stilbene comprises two aromatic rings joined by an ethylene bridge. Compound of present interest a tri-hydroxystilbene, more preferably 3,5,4'-trihdyroxystilbene, which is also known as resveratrol.

Resveratrol is found in either the cis form or trans form. Derivatives of resveratrol refers to compounds in which one or two of the hydroxyl functions of resveratrol are replaced with other moieties such as, for example, pterostilbene in which the hydroxyl functions at positions 3 and 5 on the disubstituted aromatic ring are methoxylated. Another example is .beta.-glucoside derivative polydatin or piceid, in which one of the hydroxyl functions on the disubstituted aromatic ring is replaced with glucose; as well as polymers of the parent compound resveratrol. Such polymers have been given the name viniferins.

Resveratrol is a stilbene compound, a phytoalexin (group of compounds that are produced during times of environmental stress or pathogenic attack) and a polyphenolic compound present in human dietary material such as grape skins (Soleas et al. (1995) Am. J. Enol. Vitic. 46(3):346-352), groundnuts, eucalyptus, and in at least 72 plant species, distributed in 31 genera and 12 families. Fresh grape skin contains about 50 to 100 mcg of resveratrol per gram, and the concentration in red wine is in the range of 1.5 to 3 mg/liter. It is widely considered to possess cardiovascular protective properties and has also been shown to be chemopreventive against various stages of chemically induced carcinogenesis. (*Cancer Lett* 2000 Jun. 1; 154(1):29-37 DNA breakage by resveratrol and Cu (II): reaction mechanism and bacteriophage inactivation. Ahmad A, Farhan Asad S, Singh S, Hadi S M)

In vitro and animal experiments have shown that resveratrol possesses many biological attributes that favor protection against atherosclerosis, including antioxidant activity, modulation of hepatic apolipoprotein and lipid synthesis, inhibition of platelet aggregation as well as the production of pro-atherogenic eicosanoids by human platelets and neutrophils.

Resveratrol was found to inhibit herpes simplex virus types 1 and 2 (HSV-1 and HSV-2) replication in a dose-dependent, reversible manner. (Docherty J J, et al., *Antiviral Res* 1999 October; 43(3):145-55).

Growth of the bacterial species *Staphylococcus aureus, Enterococcus faecalis*, and *Pseudomonas aeruginosa* was inhibited at 171-342 microg/mL of resveratrol in the solvent dimethyl sulfoxide. Activity against the fungal species *Trichophyton mentagrophytes, Trichophyton tonsurans, Trichophyton rubrum, Epidermophyton floccosum*, and *Microsporum gypseum* was also tested. The growth of dermatophytes was inhibited at 25-50 microg/mL of resveratrol (Chan M M *Biochem Pharmacol* 2002 Jan. 15; 63(2):99-104).

Docherty applied for US patent on a method of reducing or inhibiting the growth of *Neisseria gonorrhea* and *Neisseria meningiditis* in vitro and in vivo by using tri-hydroxylated stilbene. [US patent application 20010020043]

Methods for producing the hydroxylated stilbenes are described in Moreana-Manas, M. et al., *Anal Quim* (1985) 81:157-161; Jeandet, P. et al., *Am J. Enol Vitic* (1991) 42:41-6; Goldberg D M et al. *Anal Chem* (1994) 66:3959-63, Murakami, S et al., *Biochem Pharmacol.* (1992) 44:1947-51; and Thakkar, K et al., *J. Med Chem* (1993) 36:2650-51, which are incorporated herein by reference. Resveratrol and 3,3',4,5'-tetrahydroxy-trans-stilbene, known as piceatoannol, are also available commercially from Sigma Chemical Co., St. Louis, Mo.

Next provided is a deglycyrrhizinated *glycyrrhiza* extract obtained from the deglycyrrhizinated *glycyrrhiza* extracts. These extracts include *Glycyrrhiza Glabra, G. Kansuesis,* and *G. Inflata.*

The *Glycyrrhiza* species (Licorice) has a long and highly varied record of uses. It still remains as one of the most important herbs in traditional Indian and Chinese medicine. Among its most consistent and important uses are as a demulcent (soothing, coating agent) in the digestive and urinary tracts, to help with coughs, to soothe sore throats, and as a flavoring. It has also been used to treat conditions ranging from diabetes to tuberculosis.

The two most important constituents of licorice are glycyrrhizin and flavonoids. Glycyrrhizin breaks down to glycyrrhizic or glycyrrhetinic acid; glycyrrhizin is an anti-inflammatory and inhibits the breakdown of the cortisol produced by the body (Steinberg D, Sgan-Cohen H D, Stabholz A, et al. The anticariogenic activity of glycyrrhizin: Preliminary clinical trials. Isr J Dent Sci 1989; 2:153 B5; Soma R, Ikeda M, Morise T, et al. Effect of glycyrrhizin on cortisol metabolism in humans. Endocrin Regulations 1994; 28:31 B4). Glycyrrhizinic acid is known to aggravate hypertension, irritate the kidney and hence deglycyrrhizinated form (DGL) is in use.

Licorice flavonoids, as well as the closely related chalcones, help digestive tract cells heal. They are also potent antioxidants and work to protect the cells of the liver. In test tubes, the flavonoids have been shown to kill *Helicobacter pylori*, the bacteria that cause most ulcers and stomach inflammation.

People with eczema improved with application of an ointment with pure glycyrrhetinic acid, which was as effective as hydrocortisone, according to one clinical study (Evans F Q. The rational use of glycyrrhetinic acid in dermatology. *Br J Clin Pract* 1958; 12:269B74).

Herpes virus is inhibited by glycyrrhizic acid in test tubes (Pompei R, Flore O, Marccialis M A, et al. Glycyrrhizic acid inhibits virus growth and inactivates virus particles. *Nature* 1979; 281:689 B90).

Dehpour A R et al. (*J Pharm Pharmacol* 1994 February; 46(2):148-9) reported the protective effect of liquorice components and their derivatives against gastric ulcer induced by aspirin in rats.

Russell R I et al. (*Scand J Gastroenterol Suppl* 1984; 92:97-100) reported protective effect of deglycyrrhinised liquorice against aspirin (ASA) and ASA plus bile acid-induced gastric mucosal damage, and ASA absorption in rats. DGL diminished ASA (128 mg/kg)-induced gastric mucosal damage Endoscopic examination in 32 cases of chronic duodenal ulceration treated with deglycyrrhizinized liquorice tablets showed that healing of the ulceration had occurred and in the majority the mucosa appeared normal (Larkworthy W et al *Practitioner* 1975 December; 215 (1290):787-92)

U.S. Pat. No. 6,319,523 issued to Zhou discloses a method for inhibiting oral bacteria by using polyphenol derivative composition consisting of mogroside derivative licorice extract.

*Glycyrrhiza glabra* related spp. includes *G. kansuesis, G. inflata.*

Next provided is a *Centella* extract. The *Centella* extract is obtained from a source which is a member of the group of sources that includes asiaticoside, madecaccoside, centelloside, centoic acid and centellic acid.

*Centella asiatica* (gotu kola) has been important in the medicinal systems of India for centuries. Numerous skin diseases, ranging from poorly healing wounds to leprosy, have been treated with *centella*.

Primary active constituents of *Centella* include saponins (also called triterpenoids), known as asiaticoside, madecassoside and madasiatic acid (Kartnig T. Clinical applications of *Centella asiatica* (L) Urb. In *Herbs, Spices, and Medicinal Plants: Recent Advances in Botany, Horticulture, and Pharmacology*, vol. 3., ed. LE Craker, JE Simon. Phoenix, Ariz.: Oryx Press, 1986, 145B73).

The ratio of madecassic acid to asiaticoside varies between 1.5 and 2.3 to 1.

These saponins beneficially affect collagen (the material that makes up connective tissue), for example, inhibiting its production in hyperactive scar tissue. One uncontrolled study in humans found that a gotu kola extract helped heal infected wounds (unless they had reached bone) (Morisset R, Cote N G, Panisset J C, et al. Evaluation of the healing activity of hydrocotyle tincture in the treatment of wounds. *Phytother Res* 1987; 1:117 B21).

*Centella* extract acts on fibroblast cells and equilibrates collagen fiber synthesis. The overall effect contributes to the restoration of elastic connective tissue, a reduction in fibrosis and a shortening in the time necessary for wound healing (*Centellae asiaticae* extractum, summary report, Committee for veterinary medicinal products, The European Agency for the Evaluation of Medicinal Products, September 1998).

Topical gotu kola can help burns and wounds (Kartnig T. Clinical applications of *Centella asiatica* (L) Urb. In *Herbs, Spices, and Medicinal Plants: Recent Advances in Botany, Horticulture, and Pharmacology*, vol. 3., ed. L E Craker, J E Simon. Phoenix, Ariz.: Oryx Press, 1986, 145B73).

Double-blind studies have also shown that *Centella* extract can help those with chronic venous insufficiency (Mahajani S S, Oberai C, Jerajani H, Parikh K M. Study of venodynamic effect of an Ayurvedic formulation of *Centella asiatica* using venous occlusion plethysmography (VOP) and laser-Doppler velocimetry (LVD). *Can J Physiol Pharmacol* 1994; 72(suppl 1):180; Pointel J P, Boccalon H, Cloarec M, et al. Titrated extract of *Centella asiatica* (TECA) in the treatment of venous insufficiency of the lower limbs. *Angiology* 1986; 37(5):420B1).

*Centella* extract was helpful for preventing and treating enlarged scars (keloids) (Bossé JP, Papillon J, Frenette G, et al. Clinical study of a new antikeloid drug. *Ann Plastic Surg* 1979; 3:13 B21).

Next provided is a polyphenol-rich plant extract which is obtained from the group of polyphenol-rich plant extracts which includes the *Camellia* species. The *Camellia* species is a source of purified polyphenol. Purified phenol is a member of the group of purified phenol that includes (−) Epicatechin, (−) Epigallocatechin, (−) Epicatechin gallate, and (−) Epigallocatechin gallate.

Traditionally *Camellia sinensis* (Tea, green tea) has been used in Chinese medicine for headaches, body aches and pains, digestion, depression, immune enhancement, detoxification, as an energizer, and to prolong life. Modern research has confirmed many of these health benefits.

Green tea contains volatile oils, vitamins, minerals, and caffeine, but the active constituents are polyphenols, particularly the (−) Epicatechin, (−) Epigallocatechin, (−) Epicatechin gallate, (−) Epigallocatechin gallate. The polyphenols are believed to be responsible for most of green tea=s roles in promoting good health (Graham H N. Green tea composition, consumption, and polyphenol chemistry. *Prev Med* 1992; 21:334 B50).

Tea polyphenols, particularly ECGc is reported to have completely inhibited the growth of three strains of *P. gingivalis* and the growth of cariogenic bacteria, *S. mutans*, and *S. sobrinus* (S. Sakanaka et al. in *Chemistry and application of green tea*, ed: Takehiko, Y et al. CRC Press, 1997).

Extract of green tea leaves have been reported to show antiviral activity against herpes simplex virus, Coxsackie virus B6, and polio virus [John T et al., Virus inhibition by tea, caffeine, and tannic acid, Ind. J. med. Res. 69, 542, 1979]; rota virus and enterovirus (Mukyoyama, A et al., Inhibition of rotavirus and enterovirus infections by tea extracts, *Jpn. J. med. Sci. Biol*, 44, 181, 1991).

Extract of green tea were found to strongly inhibit *E. coli, Streptococcus salivarius* and *S. Mutans*, which are commonly found in the saliva and teeth of people suffering from dental caries (Rasheed A and Haider, M, 1998, Antibacterial activity of *Camellia sinensis* extracts against dental caries. *Arch. Pharm Res* 21(3):348-52).

Lastly provided is an *Aloe Vera* extract. The *Aloe Vera* extract is obtained from a member of the group of botanical sources of *Aloe Vera* extract that includes *A. barbadensis, A. vulgare, A. arborescens, A. ferox,* and *A. perryi.*

*Aloe Vera* has been historically used for many of the same conditions it is used for today-particularly constipation and minor cuts and burns. In India, it was also used to treat intestinal infections and suppressed menses; the root was used for colic.

Various constituents have been shown to have anti-inflammatory effects as well as to stimulate wound healing (Penneys N S. Inhibition of arachidonic acid oxidation in vitro by vehicle components. *Acta Derm Venerol Stockh* 1981; 62:59 B61).

Acemannan, the major carbohydrate fraction in the aloe gel, is a water-soluble long chain mannose polymer which accelerates wound healing, modulates immune function (particularly macrophage activation and production of cytokines) and demonstrates antineoplastic and antiviral effects (Peng S Y, et al., Decreased mortality of Norman murine sarcoma in mice treated with the immunomodulator, acemannan. *Mol. Biother.* 1991; 3:79-87; Zhang L et al., Activation of a mouse macrophage cell line by acemannan: the major carbohydrate fraction from *Aloe vera* gel. *Immunopharmacology* 1996; 35; 119-28; Rama moorthy L et al., Acemannan, a beta-(1,4)-acetylated mannan, induces nitric oxide production in macrophage cell line RAW 264.7. *Mol Pharmacol* 1996; 50:878-84).

*Aloe* gel also contains bradykininase, anti-inflammatory (Yagi A et al., Antibradykinin active material in *Aloe saponaria. J Pharmaceut Sci* 1982; 71:1172-74); magnesium lactate, which helps prevent itching, and salicylic acid and other antiprostaglandin compounds which relieve inflammation.

In vitro data confirm that aloe gel is bacteriostatic or bactericidal against a variety of common wound-infecting bacteria: *Staphylococcus aureus, S. pyogenes, Serratia marcescens, Klebsiella pneumoniae, Pseudomonas aeruginosa, E. coli, Salonella typhosa,* and *Mycobacterium tuberculosis* (Robson M et al., Myth, magic, witchcraft, or fact? *Aloe vera* revisited. *J Burn Care Rehab* 1982; 3:157-62; Lorenzetti L et al., Bacteriostatic property of *Aloe vera. J Pharmacol Sci* 1964; 53:1287; Bruce W. Investigations of the antibacterial activity in the aloe. *S Afr Med J* 1967; 41:984).

Case studies reported aloe gel applied topically could help heal radiation burns (Loveman A B. Leaf of *Aloe vera* in treatment of Roentgen ray ulcers. *Arch Derm Syph* 1937; 36:838 B43).

Some clinical studies suggest topical aloe gel for healing minor burns (Visuthikosol V, Chowchuen B, Sukwanarat Y, et al. Effect of *Aloe vera* to healing of burn wound: A clinical and histologic study. *J Med Assoc Thai* 1995; 78:403 B9).

Oral mucositis is inflammation of the mucosa of the mouth and ranges from redness to severe ulceration. The mucosa serves as an important mechanical barrier that helps to prevent a local or systemic invasion of various microbes and the absorption of microbial products that are normally present in the oral cavity and the lumen of the gut (Fink M P. Gastrointestinal mucosal injury in experimental models of shock, trauma, and sepsis. *Crit Care Med* 1991; 19:627 B41)

Other areas of the body protected by mucous membranes include gastro intestinal tract (GI), respiratory, urinary and reproductive systems.

Damage of the gastric mucosal barrier may be caused by many factors. The barrier can be damaged by non steroidal anti-inflammatory NSAIDs such as aspirin, indomethasone, ibuprofen etc, which interfere with mucus and $HCO_3$ secretion. Another major and common factor is infection of the mucosa by the bacterium *Helicobacter pylori*, which attacks and destroys mucosal cells, allowing gastric secretions to diffuse into the submucosal tissues.

Oral mucositis is also a common condition in patients with reduced immune response, such as HIV/AIDS patients.

The risk of ulcer complications, such as bleeding, perforation and death is increased approximately 4-fold in NSAID users. (Ballinger A, Smith G. COX-2 inhibitors vs. NSAIDs in gastrointestinal damage and prevention. *Expert Opin Pharmacother* 2001 January; 2(1):31-40).

Oral mucosal injury (MI) can lead to a variety of systemic consequences. These include impaired oral intake of fluid and nutrients, leading to dehydration and malnutrition, pain, nausea, vomiting, abdominal cramping, and diarrhea.

Cytotoxic chemotherapy and radiation therapy are known to cause MI both in the oral cavity (Pico J L, Avila-Garavito A, Naccache P. Mucositis: its occurrence, consequences, and treatment in the oncology setting. *Oncologist* 1998; 3:446 B51) and to mitotically active intestinal crypt cells (Baskerville A, Batter-Hatton D. Intestinal lesions induced experimentally by methotrexate. *Br J Exp Pathol* 1977; 58:663 B9). The manifestations of oral mucositis include erythema, ulcer formation, bleeding, and exudates. Methotrexate, 5-flourouracil, cisplatin cytarabine, etoposide, and radiation therapy (XRT) have been shown to have mucosal-damaging effects. Most of the patients treated for head and neck cancer and almost half of the patients receiving chemotherapy for non-head and neck cancer develop oral complications (Sonis S T. Oral complications. In: Holland J F, Bast R C Jr, Moston D L, editors. *Cancer medicine*. Baltimore (MD): Lippincott; 1997. p. 3255B64).

Slavin et al. (Slavin R E, Dias M A, Saral R. Cytosine arabinoside induced gastrointestinal toxic alterations in sequential chemotherapeutic protocols: a clinical-pathologic study of 33 patients. *Cancer* 1978; 42:1747 B59) described the natural history of cytotoxic therapy-induced intestinal damage. Initial injury began during the first week of cytotoxic therapy and was characterized by replacement of normal crypts of mucous-secreting cells by atypical undifferentiated cells. During subsequent weeks, the injury progressed to a second stage, which consisted of cellular necrosis, a lack of mitotic activity, disappearance of villous surface, and complications by various infections. Finally, the recovery phase followed, when mitotic activity returned and cells regenerated, differentiated, and covered the denuded surface.

The effect of radiation therapy on oral cavity primarily results from local tissue changes. These changes are initiated by a reduction in the proliferation of basal epithelial cells, causing atrophy (Sonis S T. Oral complications. In: Holland J F, Bast R C Jr, Moston D L, editors. *Cancer medicine*. Baltimore (MD): Lippincott; 1997. p. 3255B64). The damage of connective tissue may lead to an increase in vascular permeability and tissue edema (Baker D G. The radiobiological basis for tissue reactions in the oral cavity following therapeutic x-irradiation. A review. *Arch Otolaryngol* 1982; 108:21 B4).

Mucositis is expected to increase in frequency and severity as oncologists utilize increasingly aggressive cancer treatments in hope of achieving cure.

MI of the oral cavity is frequently accompanied by oral infections. Viral (Herpes simplex), bacterial (*Streptococcus mitis, Steptococcus oralis, Streptococcus sanguis*, vancomycin-resistant enterococci, *Stenotrophomonas maltophilia*) and fungal (*Candida* sp, *Aspergillus* sp.) infections are all common.

OM begins 5-10 days following the initiation of chemotherapy and lasts 7-14 days. Therefore, the whole process lasts 2-3 weeks in more than 90% of patients.

Oral mucositis occurs in 15-40% of patients receiving standard chemotherapy and 70% to 100% of patients receiving chemotherapy for bone marrow transplant. Furthermore, 100% of patients receiving radiation therapy for head and neck cancers are afflicted with oral mucositis.

Currently, the worldwide population of patients with mucositis is estimated at 400,000 to 600,000 patients receiving chemotherapy or radiation, with an additional 48,000 experiencing severe mucositis associated with hematopoietic stem cell transplantation. Approximately 350,000 to 400,000 patients in the United States experience mucositis resulting from these conditions.

Symptoms of mucositis vary from pain and discomfort to an inability to tolerate food or fluids. Mucositis may also limit the patient's ability to tolerate either chemotherapy or radiotherapy. Mucositis may be so severe as to delay treatment and may compromise the ultimate benefits of the treatment regimen.

Chemotherapy agents retard cell division in the oral mucosal epithelium, resulting in reduced epithelial turnover and renewal. The result is erythema from increased vascularity and epithelial atrophy 4-5 days after the initiation of chemotherapy. Microtrauma from day-to-day activities such as speech, swallowing, and mastication leads to ulceration.

During the ensuing ulcerative/bacteriological phase, putative bacterial colonization of ulcerations occurs, resulting in the flow of endotoxins into mucosal tissues and the subsequent release of more IL-1 and TNF-alpha.

World Health Organization=s grading of mucositis:

Grade Signs and Symptoms
 0 No symptoms.
 1 Sore mouth, no ulcers
 2 Sore mouth with ulcers, but able to eat normally
 3 Liquid diet only.
 4 Unable to eat or drink.

Treatment options and published studies:

The use of an allopurinol mouthwash, an oral sucralfate slurry, and pentoxifylline were reported in preliminary studies to result in a decrease in mucositis. Subsequent randomized and controlled studies, however, have failed to demonstrate any benefit to treatment with these agents (Loprinzi et al., 1995, *Sem. Oncol.* 22 Supple. 3):95-97; Epstein & Wong, 1994, *Int. J. Radiation Oncology Biol. Phys.* 28:693-698; Verdi et al., 1995, *Oral Surg. Oral Med. Oral Pathol. Oral Radiol. Endod.* 80:36-42).

Benzydamine hydrochloride, a nonsteroidal drug with analgesic and antimicrobial properties, has been studied both in patients undergoing radiation therapy and in patients receiving intra-arterial chemotherapy (Epstein et al., 1986, *Oral Surg. Oral Med. Oral Pathol.* 62:145-148; Epstein et al., 1989, *Int. J. Radiation Oncology Biol. Phys.* 16:1571-1575).

Chlorhexidine, an antimicrobial mouth rinse, has also been used extensively in the treatment and prevention of oral mucositis (Ferretti et al., 1990, *Bone Marrow Transplan.* 3:483-493; Weisdorf et al., 1989, *Bone Marrow Transplan.* 4:89-95). It has been noted however that the efficacy of chlorhexidine is significantly decreased in saliva, and that this compound is relatively ineffective against the Gram negative bacteria that tend to colonize the oral cavity in patients undergoing radiation therapy (Spijkervet et al., 1990, *Oral Surg. Oral Med. Oral Pathol.* 69:444-449). In addition, at least one study has shown that the use of chlorhexidine may be detrimental and result in a higher incidence of mucositis (Foote et al., 1994, *J. Clin Oncol.* 12:2630-2633).

Several studies have shown that the use of a vancomycin paste and antibiotic lozenges containing polymixin B, tobramycin and amphotericin B in patients undergoing myelosuppresive chemotherapy or radiation therapy can result in a decrease in oral mucositis and in the incidence of sepsis due to alpha hemolytic streptococci (Barker et al., 1995, *J. Ped. Hem. Oncol.* 17:151-155; Spijkervet et al., 1991, In: *Irradiation Mucositis*, Munksgaard Press, pp. 43-50). Clarkson J E, et al, (Clarkson J E, Worthington H V, Eden O B. Interventions for preventing oral mucositis or oral candidiasis for patients with cancer receiving chemotherapy (excluding head and neck cancer) (Cochrane Review). In: The Cochrane Library, 1, 2002) reviewed currently available treatment option to treat mucositis: a variety of mouthwashes (with benzydamine hydrochloride, corticosteroids) mixed actions have been evaluated and include benzydamine hydrochloride, Chamomile); colony stimulating factors and immunoglobulin; topical anaesthetic agents (Viscous lignocaine and xylocalne in mouthrinses);

antiseptic solutions (chlorhexidine, povidone iodine and hydrogen peroxide);

antimicrobial agents (nystatin, clotrimazole and PTA lozenges. Antibiotic lozenges); lozenges (containing polymixin E, tobramycin and amphotericin B, Acyclovir); mucosal barrier (with sucralfate); cytoprotectants (Beta-carotene, vitamin E); Candies containing capsaicin.

At present, no specific therapies are proven to be effective to either treat or prevent MI secondary to cytotoxic chemo radiotherapy (Shahab A. Khan, John R. Wingard, *Journal of the National Cancer Institute Monographs*, No. 29, 31-36, 2001)

Same conclusion has been reached by Clarkson J E et al. They evaluated the effectiveness of oral (and topical) prophylactic agents for oral mucositis and oral candidiasis in patients with cancer (excluding head and neck cancer), compared with placebo or no treatment. Of the 27 useable studies 14 had data for mucositis comprising 945 randomized patients and 15 included data for oral candidiasis with 1164 randomized patients. Reviewers concluded that none of the other prophylactic agents included in this review prevented mucositis. Of the eight prophylactic agents used for mucositis only one, ice chips, was effective. (Relative risk 0.57, 95% CI 0.43 to 0.77, chi-square for heterogeneity=0.26 (df=1), p=0.61) [Clarkson J E, Worthington H V, Eden O B. Interventions for preventing oral mucositis or oral candidiasis for patients with cancer receiving chemotherapy (excluding head and neck cancer) (Cochrane Review). In: The Cochrane Library, 1, 2002].

Most of the above treatment approaches are either single step approaches (for instance, as an anti-inflammatory or analgesic or antipyretic or antimicrobial or immunomodulatory or mucosal cell stimulant agent) or are focused on solving the problem at superficial level (like mucosal barrier or anesthetic) without addressing the totality of the problem.

A complex problem like mucositis needs a comprehensive and multi-pronged approach; for example, the solution should include in relieving the pain, repairing the mucosal lining, eliminating unwanted microbes. Single compound and single approach therapies have failed so far, as evident by the literature reviewed here.

Another aspect of currently available treatments are almost all of the drugs used are synthetic chemical entities inflicting their own side effects like dry mouth, numbness, negative effect on the taste. It is the irony that purpose of the treatment is to alleviate the side effects of chemo/radio therapy and such a treatment ends up causing its own side effects to the user. There is a need to develop treatment with one or more compound that are as natural as possible with minimal side effects.

It is therefore, an object of the invention to provide improved treatment for oral mucositis and other bodily mucosal disorders.

It is further an object of the invention to provide an improved treatment for the oral, pulmonary, and vaginal cavities, stomach, duodenal linings adversely affected by disease/conditions, or the injury and the pain associated therewith.

It is further an object of the invention to provide an improved treatment with comprehensive and multipronged approach of rebuilding damaged mucosal lining, minimizing pain, and eliminating microbial infections.

It is further an object of the invention to provide an improved treatment with natural compounds.

It is further an object of the invention to provide an improved treatment with minimal side effects.

It is still a further object of this invention to provide pharmaceutical compositions and dosage amounts of the pharmaceutical compositions suitable for use with such treatments.

Further and other objects of the invention will be realized by those skilled in the art from the following summary of invention and detailed description of embodiments thereof.

This invention pertains to therapeutic composition for prevention and treatment of oral mucositis and bodily mucosal disorders of mammals. More particularly, the therapeutic composition comprises one or more stilbene compounds, and a phytotherapeutic composition. This invention also pertains to methods for preparing and using the therapeutic compositions and the pharmaceutical products in which the therapeutic composition may be used.

A preferred embodiment of the phytotherapeutic composition of this invention comprises [a] deglycyrrhizinated extract obtained from botanical source selected from *Glycyrrhiza* species, in concentrated or pharmaceutically acceptable form. [b] asiaticoside-rich extract obtained from botanical source selected from the group consisting of *Centella* species, purified forms of asiaticoside, madecassoside, centelloside, centoic acid, centellic acid, pharmaceutically acceptable salts, and mixtures thereof [c] polyphenol-rich plant extracts obtained from botanical source selected from the group consisting of *Camellia* species, purified polyphenols, (−) Epicatechin, (−) Epigallocatechin, (−) Epicatechin gallate, (−) Epigallocatechin gallate, pharmaceutically acceptable salts, biological materials yielding such mentioned polyphenols in the targeted user, and mixtures thereof. [d] *Aloe vera* gel, extract; wherein components a, b, c, d are present in amounts sufficient to synergistically enhance treatment of oral mucositis and other bodily mucosal disorders This invention pertains to therapeutic composition for the prevention and treatment of oral mucositis and other bodily mucosal disorders. The composition of the present invention has been found to be effective prevention and treatment of oral mucositis and bodily mucosal disorders.

In accordance with the present invention, a composition is provided which preferably includes [A] a therapeutically effective amount of at least one stilbene compound and a phytotherapeutic composition which comprises: [a] deglycyrrhizinated extract obtained from botanical source selected from *Glycyrrhiza* species, in concentrated or pharmaceutically acceptable form. [b] asiaticoside-rich extract obtained from botanical source selected from the group consisting of *Centella* species, purified forms of asiaticoside, madecassoside, centelloside, centoic acid, centellic acid, pharmaceutically acceptable salts, and mixtures thereof. [c] polyphenol-rich plant extracts obtained from botanical source selected from the group consisting of camellia species, purified polyphenols, (−) Epicatechin, (−) Epigallocatechin, (−) Epicatechin gallate, (−) Epigallocatechin gallate, pharmaceutically acceptable salts, materials yielding these mentioned polyphenols as end products in the targeted mammal, and mixtures thereof. [d] *Aloe vera* gel, extract; wherein components a, b, c, d, are present in amounts sufficient to synergistically enhance treatment of oral mucositis and other bodily mucosal disorders.

Each component of the composition of the present invention has been found to provide a particular effect, and the combination provides a synergistic effect, which inhibits all the three types of microbial infections: bacteria, virus and fungus; diminishes mucosal damage, heals; renews mucosa; and minimizes pain.

The stilbene component of the present invention is selected from the group consisting of polyhydroxylated stilbene; a polyhydroxylated stilbene and preferably is resveratrol or a derivative thereof, or a biological or chemical compound yielding to such resveratrol in the target mammal. Suitable resveratrol can be obtained from dietary material such as grape skins, groundnuts, eucalyptus, *Polygonum cuspidatum* and other plant species, at least 72 plant species, distributed in 31 genera and 12 families. Other plants with stilbene compounds include *Piper methysticum, Pinus resinosa, Saccharum officinarum, Morus alba, Marchantia polymorpha, Orchis militaris.*

Resveratrol can be cis-resveratrol, trans-resveratrol, a mixture thereof, or a pharmacologically acceptable salt, ester, amide, prodrug or analog thereof.

Trans-resveratrol can be synthesized from appropriately substituted phenols by means of a Wittig reaction modified by Waterhouse from the method of Moreno-Manas and Pleixats. The final product is greater than approximately 95% pure as may be confirmed using NMR and UV spectroscopy. Trans-resveratrol can be converted to the cis isomer by preparing a solution of the trans isomer in a suitable solvent, e.g., 0.2 M phosphoric acid-acetonitrile (4:1 v/v). The solution is then irradiated for 5-10 min at a wavelength of 254 nm and an intensity of 990 $\mu$LW/$cm^2$. Ultraviolet spectroscopy will confirm that the trans-resveratrol peak, at 306 nm, to be substantially reduced following this procedure. (See Goldberg et al. 1995 *J. Chromatog.* 708:89-98.)

The stilbene compound is present in the therapeutic composition in an amount from about 0.001 to about 10%, by weight of the therapeutic composition.

Extract of *Glycyrrhiza* species must be deglycyrrhizinated to prevent unwanted side effects. Other species of *Glycyrrhiza* include, but not limited to *G. kansuesis, G. inflata.* Active components of *Glycyrrhiza* can be extracted with alcohol and other acceptable solvents. Licorice flavonoids, as well as the closely related chalcones, help digestive tract cells heal. They are also potent antioxidants and work to protect the cells of the liver.

Deglycyrrhizinated extract of *Glycyrrhiza* species is present in the therapeutic composition in an amount from about 0.01 to about 40%, by weight of the therapeutic composition.

Primary active constituents of *Centella* include saponins (also called triterpenoids), known as asiaticoside, madecassoside and madasiatic acid. These saponins beneficially affect collagen (the material that makes up connective tissue), for example, inhibiting its production in hyperactive scar tissue.

Asiaticoside-rich extract selected from the group consisting of *Centella* species is present in the therapeutic composition in an amount from about 0.01 to about 20%, by weight of the therapeutic composition.

The composition of the present invention preferably includes-polyphenol-rich plant extracts from the group consisting of *Camellia* species, purified polyphenols, (−) Epicatechin, (−) Epigallocatechin, (−) Epicatechin gallate, (−) Epigallocatechin gallate, pharmaceutically acceptable salts, biological materials yielding such mentioned polyphenols in the targeted user, and mixtures thereof. Green tea contains volatile oils, vitamins, minerals, and caffeine, but the active constituents are polyphenols, particularly the (−) Epicatechin, (−) Epigallocatechin, (−) Epicatechin gallate, (−) Epigallocatechin gallate.

Tea polyphenols, particularly ECGc reported to have completely inhibited the growth of three strains of *P gingivalis*. Extract of green tea were found to strongly inhibit *E. coli, Streptococcus salivarius* ands. Mutans, which are commonly found in the saliva and teeth of people suffering from dental caries.

Composition (%) of "crude catechins" in green tea: (+)-Gallocatechin (GC) 1.44; (−)-Epigallocatechin (EGC) 17.57; (−)-Epicatechin (EC) 5.81; (−)-Epigallocatechin gallate (EGCg) 53.90; (−)-Epicatechin gallate (ECg) 12.51/91.23.

Polyphenol-rich plant extracts from the group consisting of *Camellia* species is present in the therapeutic composition in an amount from about 0.01 to about 15%, by weight of the therapeutic composition.

Various constituents of *Aloe vera* have been shown to have anti-inflammatory effects as well as to stimulate wound. Acemannan, the major carbohydrate fraction in the aloe gel, is a water-soluble long chain mannose polymer which accelerates wound healing, modulates immune function.

In vitro data confirm that aloe gel is bacteriostatic or bactericidal against a variety of common wound-infecting bacteria: *Staphylococcus aureus, S. pyogenes, Serratia marcescens, Klebsiella pneumoniae, Pseudomonas aeruginosa, E. coli, Salonella typhosa*, and *Mycobacterium tuberculosis*

Aloe species include *A. barbadensis, A. vulgare, A. arborescens, A. ferox, A. perryi*.

Aloe gel, extract is present in the therapeutic composition in an amount from about 1 to about 15%, by weight of the therapeutic composition.

In accordance with the present invention, each of the components of the present composition have been found to exhibit independently, one or more properties desirable in this context, including controlling bacteria, controlling virus, controlling fungus, wound healing, regeneration of diminished mucosa, renewal of mucosa; however, the effect is dramatically increased when they are combined. Multitask effect is very desirable in the prevention and treatment of mucositis.

Pharmaceutical formulations can be prepared by procedures known in the art. For example, the therapeutic composition can be formulated with common excipients, diluents, or carriers, and formed into tablets, capsules, sprays, mouth washes, lozenges, suspensions, powders, and the like. Examples of excipients, diluents, and carriers that are suitable for such formulations include the following: fillers and extenders such as starch, modified starches, sugars, sugar-alcohols, and silica derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols. The therapeutic composition can also be formulated as elixirs or solutions for convenient oral administration or as solutions appropriate for parenteral administration, for instance by intramuscular, subcutaneous or intravenous routes. The formulations can be so constituted that they release the active ingredient only or preferably in a particular part of the intestinal tract, possibly over a period of time. The coatings, envelopes, and protective matrices may be made, for example, from polymeric substances or waxes. Lozenges are the medicinal agent in a suitably flavored base. The base may be a hard sugar candy, sugar-alcohol candy, glycerinated gelatin, or the combination of sugar with sufficient mucilage to give it form. Hard boiled candies can also be made with the therapeutic composition. Syrup is concentrated to the point where it becomes a pliable mass, the therapeutic composition is added, and the mixture is kneaded while warm to form a homogeneous mass. The mass is gradually worked into a pipe form having the diameter desired for the candy piece and the candies are cut from the pipe and allowed to cool.

Chewable wafers can also be prepared without applying heat to the therapeutic composition. The granulation is prepared in a manner similar to that used for any compressed tablet. The wafer is made using heavy compression equipment to give a tablet, which is harder than usual as it is desirable for the wafer to dissolve or disintegrate slowly in the mouth. Therapeutic composition can also be made in to a mouth wash.

Formulation 1: Gelatin Capsules

Hard gelatin capsules are prepared using the following:

| Ingredient | Quantity (mg/capsule) |
| --- | --- |
| Therapeutic composition | 0.1-700 |
| Magnesium stearate | 0-20 |
| Silica | 0-10 |

The ingredients are blended, passed through a No. 45 mesh U.S. sieve, and filled into hard gelatin capsules.

The specific formulations above may be changed in compliance with the reasonable variations provided. A tablet formulation is prepared using the ingredients below:

Formulation 2: Tablets

| Ingredient | Quantity (mg/tablet) |
| --- | --- |
| Therapeutic composition | 0.1-1000 |
| Cellulose, microcrystalline | 0-650 |
| Silicon dioxide, fumed | 0-10 |
| Stearate acid | 0-20 |

The components are blended and compressed to form tablets. Alternatively, sugar-free chewable wafer tablets are made up as follows:

Formulation 3: Sugar-Free Chewable Wafer Tablets

| Ingredient | Quantity (mg/tablet) |
| --- | --- |
| Therapeutic composition | 0.1-1000 |
| Sorbitol | 1000-1500 |
| Magnesium stearate | 20 |
| Stearic acid | 40 |
| Flavor | 10 |
| Artificial sweetener | 1-3 |
| Soluble gum | 50-100 |

The ingredients are blended in a V-blender for 25 minutes and are compressed on a tablet machine to yield tablets.

Suspensions are made as follows:

Formulation 4: Suspensions

| Ingredient | Quantity (mg/5 ml) |
| --- | --- |
| Therapeutic composition | 0.1-1000 mg |
| Sodium carboxymethyl cellulose | 50 mg |
| Syrup | 1.25 mg |
| Benzoic acid solution | 0.10 mL |
| Flavor | q.v. |

| Ingredient | Quantity (mg/5 ml) |
| --- | --- |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 5: Nasal Solution

| Ingredient | Quantity (mg/5 ml) |
| --- | --- |
| Therapeutic composition | 0.1-1000 mg |
| Chlorobutanol | 0.5 g |
| Sodium Chloride | 0.5 g |
| Water | to 100 ml |

Formulation 6: Mouth Wash

| Ingredient | Quantity (%) |
| --- | --- |
| Therapeutic composition | 0.1-30 |
| Alcohol | 10-20 |
| Sorbitol | 1-10 |
| Flavoring | 1-5 |
| Benzoic acid | 0.1 |
| Sodium benzoate | 0.1 |
| Artificial sweetener | 0.1-1 |
| Water | to 100 |

Augmented therapeutic composition tablets are made up as follows:

Formulation 7: Augmented Therapeutic Composition Tablets

| Ingredient | Quantity (mg/tablet) |
| --- | --- |
| Therapeutic composition | 0.1-1000 |
| l-arginine (Nintric oxide-donor) | 500-1000 |
| Sorbitol | 1000-1500 |
| Magnesium stearate | 20 |
| Stearic acid | 40 |
| Flavor | 10 |
| Artificial sweetener | 1-3 |
| Soluble gum | 50-100 |

The ingredients are blended in a V-blender for 25 minutes and are compressed on a tablet machine to yield tablets.

Formulation 8: Augmented Therapeutic Composition Tablets with Cooling Effect

| Ingredient | Quantity (mg/tablet) |
| --- | --- |
| Therapeutic composition | 0.1-1000 |
| Menthyl lactate | 1-10 |
| Sorbitol | 1000-1500 |
| Magnesium stearate | 20 |

-continued

| Ingredient | Quantity (mg/tablet) |
| --- | --- |
| Stearic acid | 40 |
| Flavor | 10 |
| Artificial sweetener | 1-3 |
| Soluble gum | 50-10 |

Assay

Five to twenty patients are selected for clinical study. The patients are set to undergo either chemo or radiotherapy, which will induce oral mucositis. The study has a placebo control group, which would receive formula #3 chewable wafers with no therapeutic composition. Patients in the test group will receive chewable wafer with 400-600 mg. therapeutic composition. One week prior to chemotherapy, patients will chew three tablets daily and continue during the therapy and two months beyond. Number and severity of symptoms in both the groups and at the end of the study the results are compared. Utility of the therapeutic compound is illustrated by the positive impact they have in this assay.

Five to twenty patients are selected for clinical study. The patients are with stomach ulcer. The study has a placebo control group, which would receive formula #3 chewable wafers with no therapeutic composition. Patients in the test group will receive chewable wafer with 400-600 mg. therapeutic composition. Patients will chew two tablets thrice-daily and continue for four weeks. Number and severity of symptoms in both the groups and at the end of the study the results are compared. Utility of the therapeutic compound is illustrated by the positive impact they have in this assay.

Attached hereto as an Appendix are the clinical data and report.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A therapeutic composition comprising:
   a deglycyrrizinated *glycyrrhiza* extract,
   a *Centella* extract,
   an Angelica Root extract,
   a green tea extract,
   a stilbene compound, and
   an *Aloe* extract wherein said composition is in a dissolvable wafer.

2. A therapeutic composition as described in claim 1 wherein the stilbene compound is a polyhydoxylated stilbene.

3. A therapeutic composition as described in claim 2 wherein the polyhydroxylated stilbene is resveratrol.

4. A therapeutic composition as described in claim 1 wherein the degycyrrhizinated *glycyrrhiza* extract is selected from the group consisting of *Glycyrrhiza Glabra*, *Glycyrrhiza Kansuesis* and *Glycyrrhiza Inflata*.

5. A therapeutic composition as described in claim 1 wherein the *Centella* extract is a *Centella asiatica* extract.

6. The composition as set forth in claim 1 wherein the composition further contains a polyphenol-rich plant extract which is obtained from a plant from the group consisting of *Areca catechu*, *Potentilla fragariodes*, *Ginko biloba* and *Angelia sinensis*.

7. The composition as set forth in claim 1 wherein the *aloe* extract is *aloe vera*.

8. The composition as set forth in claim 7 wherein the *aloe vera* is obtained from a member of the group consisting of *Aloe vulgare*, *Aloe arborescens*, *Aloe ferox* and *Aloe perryi*.

9. The composition as set forth in claim 1 wherein the stilbene compound is present in the therapeutic composition in an amount from about 0.001 to about 10 percent by weight of the therapeutic composition.

10. The composition as set forth in claim 1 wherein the deglycyrrhizinated *Glycyrrhiza* extract is present in the therapeutic composition in an amount from about 0.01 to about 40 percent by weight of the therapeutic composition.

11. The composition as set forth in claim 1 wherein the *Centella* extract is present in the therapeutic composition in an amount from about 0.01 to about 20 percent by weight of the therapeutic composition.

12. The composition as set forth in claim 1 wherein the polyphenol-rich plant extract is present in the therapeutic composition in an amount from about 0.01 to 15 percent by weight of the therapeutic composition.

13. The composition as set forth in claim 1 wherein the *Aloe* extract is present in the therapeutic composition in an amount from about 1 to about 15 percent by weight of the therapeutic composition.

\* \* \* \* \*